US007892562B2

(12) United States Patent
Karp (10) Patent No.: US 7,892,562 B2
(45) Date of Patent: Feb. 22, 2011

(54) METHODS OF INDUCING TH-1 IMMUNE RESPONSES TO HIV-1 BY ADMINISTERING UV/PSORALEN-TREATED DESIALATED INACTIVIATED HIV-1 VIRIONS DEFICIENT IN CD55 AND CD59

(76) Inventor: Nelson M. Karp, 460 S. Independence Blvd., Virginia Beach, VA (US) 23462

( * ) Notice: Subject to any disclaimer, the term of this patent is extended or adjusted under 35 U.S.C. 154(b) by 0 days.

(21) Appl. No.: 12/576,055

(22) Filed: Oct. 8, 2009

(65) Prior Publication Data
US 2010/0086566 A1 Apr. 8, 2010

Related U.S. Application Data

(60) Provisional application No. 61/195,541, filed on Oct. 8, 2008, provisional application No. 61/195,540, filed on Oct. 8, 2008, provisional application No. 61/195,539, filed on Oct. 8, 2008.

(51) Int. Cl.
*A61K 39/21* (2006.01)
*C12N 7/06* (2006.01)
(52) U.S. Cl. .................................... 424/208.1; 435/238
(58) Field of Classification Search ........................ None
See application file for complete search history.

(56) References Cited

U.S. PATENT DOCUMENTS

| 5,580,773 | A | 12/1996 | Kang et al. |
| 6,060,065 | A | 5/2000 | Barney |
| 6,627,197 | B2 | 9/2003 | Keener |
| 6,747,126 | B1 | 6/2004 | Eckert |

FOREIGN PATENT DOCUMENTS

WO    WO 9714436    4/1997

OTHER PUBLICATIONS

Azadegan, A.A. et al.; 1984; "Cohen venom factor abrogates passive humoral resistance to syphilitic Infection in hamsters"; Infec. Immun. 44(3); 740-742.
Bar et al; "Role of the Ecodomain of the gp41 Transmembrane Envelope Protein of Human Immunodeficiency Virus Type 1 in Late Steps of the Membrane Fusion Process"; Journal of Virology; Jan. 2004; pp. 811-820.
Bentz et al; "Deployment of Membrane Fusion Protein Domains During Fusion"; Cell Biology International; vol. 24, No. 11; 2000; pp. 819-838.
Bewley et al; "Design of a Novel Peptide Inhibitor of HIV Fusion that Disrupts the Internal Trimeric Coiled-coil of gp41"; The Journal of Biological Chemistry; vol. 277, No. 16, 2002; pp. 14238-14245.
Burnett M.S. et al. Potential live Vaccines for HIV, Vaccine, 2001, vol. 19, pp. 735-742.
Chan et al; "Effect of Extension of the Cytoplasmic Domain of Human Immunodeficiency Type 1 Virus Transmembrane Protein gp41 on Virus Replication"; Journal of Virology; May 2004; pp. 5157-5169.

Day et al; "The Membrane-Proximal Tyrosine-Based Sorting Signal of Human Immunodeficiency Virus Type 1 gp41 is Required for Optimal Viral Infectivity"; Journal of Virology; Feb. 2004; pp. 1069-1079.
Dey et al; "N-terminal substitutions in HIV-1 gp41 reduce the expression of non-trimeric envelope glycoproteins on the virus"; ScienceDirect; Virology 372; 2008; pp. 187-200.
Earp et al; "The Many Mechanisms of Viral Membrane Fusion Proteins"; Dept. of Microbiology; UVA; 2004; 285: pp. 25-66.
Ebenbichler et al; "The Human Immunodeficiency Virus Type 1 Transmembrane gp41 Protein is a Calcium-Binding Protein and Interacts with the Putative Second-Receptor Molecules in a Calcium-Dependent Manner"; Journal of Virology, Mar. 1996; pp. 1723-1728.
Evans, D.J. et al. An engineered poliovirus chimaera elicits broadly reactive HIV-1 neutralizing antibodies. Nature. Jun. 1, 1989, vol. 339, pp. 385-388 (abstract only).

He et al; "Conserved Salt-bridge between the N- and C-Terminal Heptad Repeat Regions of HIV-1 gp41 Core Structure is Critical for Virus Entry and Inhibition"; Journal of Virology, 2008; pp. 1-41.

Honda, M. et al. Protective immune responses induced by secretion of a chimeric soluble protein from a recombinant Mycobacterium *Bovis bacillus* Calmette-Guerin vector candidate vaccine for human immunodeficiency virus type 1 in small animals. Proc. Natl. Acad. Sci. Nov. 1995, vol. 92, pp. 10693-10697 entire document.

Jiang et al; "Maturation-Dependent Human Immunodeficiency Virus Type 1 Particle Fusion Requires a Carboxyl-Terminal Region of the gp41 Cytoplasmic Tail"; Journal of Virology, 2007; pp. 9999-10008.

Kim et al; "Leucine Zipper Domain of HIV-1 gp41 Interacted Specifically with α-Catenin"; Biochemical and Biophysical Research Comunications 291; 2002; pp. 1239-1244.

Kingsman, A. J. et al. Yeast retrotransposon particles as antigen delivery systems. Ann. NY Acad. Sci. May 31, 1995, vol. 754, pp. 202-213 (abstract only).

(Continued)

*Primary Examiner*—Jeffrey S. Parkin
(74) *Attorney, Agent, or Firm*—Williams Mullen

(57) ABSTRACT

Administration protocols for a fusion protein, matrix protein and psoralen inactivated HIV based immunogenic composition that induces an immune response to HIV. The immunogenic compositions are based on HIV biologically active fusion peptide, matrix peptide, or psoralen inactivated HIV. The number of doses is 3X. The starting dose for an adult is $1x10^9$-$1x10^{10}$. The starting dose for an adolescent is ½($1x10^9$-$1x10^{10}$). The starting dose for a pediatric patient is ¼($1x10^9$-$1x10^{10}$). The second dose will consist of $1/10^{th}$ of starting concentrations. The third dose will consist of $1/100^{th}$ of starting concentrations. This will facilitate a Th-1 response. The days of administration are days 1; 30; and 180. Alternatively the days of administration are days 1; 20-40; and 160-200. The site of administration is one that targets lymphatic tissue. Adjuvant is administered before, simultaneous with or after each dose of the immunogenic compositions. Adjuvants are used to promote a Th-1 immune response and include a leukotriene receptor antagonist such as Montelukast, a mast cell and basophil stabilizer such as Cromolyn, and a prostaglandin synthetase inhibitor such as Indomethacin. Th-1 immune responses to the immunogenic compositions are monitored. The 3X cycle will repeat on until a Th-1 immune response is observed. At that point, the immunogenic composition administered could then decline by a factor of 10 for two more vaccination procedures.

12 Claims, 2 Drawing Sheets

OTHER PUBLICATIONS

Kobasha et al; "The Prefusogenic Intermediate of HIV-1 gp41 Contains Exposed c-peptide Regions"; The Journal of Biological Chemistry; vol. 278; No. 9; 2003; pp. 7573-7579.

LeDuc et al; "Insights into a Structure-Based Mechanism of Viral Membrane Fusion"; Bioscience Reports; vol. 20, No. 6; 2000; pp. 557-570.

Lopez-Verges et al; "Tail-interacting protein TIP47 is a connector between Gag and Env and is required for Env incorporation into HIV-1 virions"; PNAS, vol. 103, No. 40; Oct. 3, 2006; pp. 14947-14952.

Maggioni et al; "Synthesis and Quality Control of Viral Membrane Proteins"; CTMI 285; 2004; pp. 175-198.

Marti et al; "Fast Folding of the HIV-1 and SIV gp41 Six-helix Bundles"; J. Mol. Biol. 336; 2004; pp. 1-8.

Mata, M. et cl., 2001, "Evaluation of a recombinant Listeria monocytogenes expressing an HIV protein that protects mice against viral challenge"; Vaccine 19:1435-1445.

Murakami et al; "The long cytoplasmic tail of gp41 is required in a cell type-dependent manner for HIV-1 envelope glycoprotein Incorporation into virions"; PNAS; vol. 97, No. 1; Jan. 4, 2000; pp. 343-348.

Murakami et al; "Genetic Evidence for an Interaction between Human Immunodeficiency Virus Type 1 Matrix and α- Helix 2 of the gp41 Cytoplasmic Tail"; Journal of Virology; Apr. 2000; pp. 3548-3554.

Noah et al; "The Membrane Proximal External Region of the HIV-1 Envelope Glycoprotein gp41 Contributes to the Stabilization of the Six-Helix Bundle formed with a Matching N' Peptide"; Biochemistry; 47(26); Jul. 1, 2008; pp. 6782-6792.

Poumbourios et al; "Determinants of Human Immunodeficiency Virus Type 1 Envelope Glycoprotein Oligomeric Structure"; Journal of Virology; Feb. 1995; pp. 1209-1218.

Poumbourios et al; "Human Immunodeficiency Virus Type 1 Envelope Glycoprotein Oligomerization Requires the gp41 Amphipathic α-Helical/Leucine Zipper-Like Sequence"; Journal of Virology; Mar. 1997; pp. 2041-2049.

Quintana et al; "HIV-1 fusion peptide targets the TCR and inhibits antigen-specific T cell activation"; The Journal of Clinical Investigation; vol. 115, No. 8; Aug. 2005; pp. 2149-2158.

Rayevskaya, M. et al. Anti-human immunodeficiency virus-gag CD8+memory T cells generated in virto from Listeris-immunized mice. Immunology, 2003, vol. 109, pp. 450-460.

Roux et al; "AIDS virus envelope spike structure"; Current Opinion in Structural Biology; 2007; 17: pp. 244-252.

Sackett et al; "The HIV Fusion Peptide Adopts Intermolecular Parallel β-Sheet Structure in Membranes when Stablized by the Adjacent N-Terminal Heptad Repeat: A $^{13}$C FTIR Study"; J. Mol. Biol. 350: 2005; pp. 790-805.

Schroeder et al; "Influenza A Virus M2 Protein: Proton Selectivity of the Ion Channel, Cytotoxicity, and a Hypothesis on Peripheral Raft Association and Virus Budding"; Viral Membrane Proteins: Structure, Function, and Drug Design; 2005; pp. 113-130.

Sham et al; "Solution Structure of a Calmodulin-Binding Domain in the Carboxy-Terminal Region of HIV Type 1 gp160"; Aids Research and Human Retroviruses; vol. 24, No. 4; 2008; pp. 607-616.

Shnaper et al; "The C-and the N-Terminal Regions of Glycoprotein 41 Ectodomain Fuse Membranes Enriched and Not Enriched with Cholesterol, Respectively"; The Journal of Biological Chemistry; vol. 279, No. 18, Apr. 2004; pp. 18526-18534.

Srinivast et al; "Cytosolic Domain of the Human Immunodeficiency Virus Envelope Glycoproteins Binds to Calmodulin and Inhibits Calmodulin-regulated Proteins"; The Journal of Biological Chemistry; vol. 268, No. 30, Oct. 1993; pp. 22895-22899.

Wyma et al; "Coupling of Human Immunodeficiency Virus Type 1 Fusion to Virion Maturation: a Novel Role of the gp41 Cytoplasmic Tail", Journal of Virology; Apr. 2004; pp. 3429-3435.

Discipio, R. G., "Ultrstructures and interactions of compelement factors H and I" J. Immunology, vol. 149, ISS 8, pp. 2592-2599 (1992).

Fearon, D.T., et al., "Activation of the alternative complement pathway due to resistence of zymosan-bound amplification convertase to endogenous regulatory mechanisms," . . . - Proc. Natl. Acad. Sci. vol. 74, No. 4 pp. 1683-1687 (Apr. 1977).

Feifel, Elisabeth, et al., "Polymorphism and deficiency of human factor H-related proteins p39 and p37," Immunogenetics, vol. 36, pp. 104-109 (1992).

Fishelson, Z., et al., C3 Convertase of Human Complement: Enhanced Formation and Stability of the Enzyme generated with Nickel instead of Mafnesiurn,: J. of Immun., vol. 129,. CONT- No. 6, pp. 2603-2607 (Dec. 1982).

Forrest, Bruce D., et al., "Effect of Parenteral Immunization on the Intestinal Immune Response to Salmonella typhy Ty21a," Infection and Immunity. Col. 60, No. 2, pp. 465-471 (Feb. 1992).

Franke, E.K., et al.,"Chaperoning a pathogen," Nature, 372 (6504) 319-20 (Nov. 24, 1994).

Franke, E.K., et al., "Specific Incorporation of Cyclophilin A into HIV-1 Virions," Nature, 372(6504): 359 (Nov. 1994).

Chan, D.C. et al., "core Structure of gp41 from the HIV Envelope Glycoprotein" Cell, vol. 89, Issue 2, pp. 263-273 (Apr. 18, 1997).

Chen, Chien-Hung, et al., "Enhancement of DNA Vaccine Potency by Linkage of Antigen Gen to an HSP70 Gene," Cancer Research 60: 1035-1042 (Feb. 15. 2000).

Cheng, Wen-Fang, et al., "Tumor-specific immunity and antiangiogenisus generated by a DNA vaccine encoding calreticulin linked to a tumor antigen," Journal of Clinical . . . -Investigation, vol. 108, No. 5, 669-678 (Sep. 2001).

Hung - Chien-Fu, et al., "Enhancing Major Histocompatibility Complex Class 1 Antigen Presentation by Targeting Antigen to Centrosomes," Cancer Research 63: 2393-2398. (May 15, 2003).

Cohen, P.T., The AIDS Knowledge Base, 15-18, 21 (3rd ed. 1999).

Cummins, Melissa, et al., New Research Uncovers Potential for More Effective Anti-HIV Therapies: Essential Role of Cyclophilin, Novel Non-Mutable Drug Target Discovered, CONT -PR NewsWire 1996.

Dierich, M. P., et al., "HIV and human complelent: mechanisms of interaction and biological implications," Immunology Today, vol. 14, Iss 9, pp. 435-440 (1993).

Dutch Rebecca Ellis, et al: "Virus Membrane Fusion Proteins: Biological Machines that Undergo a Metamorphosis" Bioscience Reports, vol. 20, No. 6, Dec. 2000, pp. 597-612, XP009012078, ISSN: 0144-8463.

Hart M K, et al: "Priming of Anti-Human Immunodeficiency Virus HIV CD8 Positive Cytotoxic T Cells in0Virto by Carrier-FreeHIV Synthetic Peptides" Proceedings of the National Academy of Sciences of the United States of America, vol. 88, No. 21, 1991, pp. 9448-9452, XP002485345, ISSN: 0027-8424.

Louis J M, et al: "Design and Properties of Nccg-gp41, a Chimeric gp41 Molecule with Nanomolar HIV Fusion Inhibitory Activity" Journal of Biological Chemistry, AI, vol. 276, No. 31, Aug. 3, 2000, pp. 29485-29489, XP002201626, ISSN: 0021-9258, pp. 29487-8.

Pinter C, et al: "Interference with Comlement Regulatory Molecules as a Possible Therapeutic Startegy in HIV Infection" Expert Opinion on Investigation Drugs Feb. 2000, vol. 9, No. 2, Feb. 2000, pp. 199-205, XP002484637, ISSN: 1354-3784, p. 202.

Honda, M., et al. Protective immune responses induced by secretion of a chimeric soluble protein from a recombinant Mycobacterium Bovis bacillus Calmette-Guerin vector candidate vaccine for human Immunodeficiency virus type 1 in small animals, Proc. Natl. Acad. Sci. Nov. 1995, vol. 92, pp. 10693-10697 entire document.

Evans, D.J. et al. An engineered poliovirus chimaera elicits braodly reactive HIV-1 neutralizing antibodies Nature. Jun. 1, 1989, vol. 339, pp. 385-388 (abstract only).

Rayevskaya, M. et al. Anti-human immunodeficiency virus-gag CD8+memory T cells generated in vitro from Listeris-immunized mice. Immunology, 2003, vol. 109, pp. 450-460, entire document.

Burnett, M.S. et al. Potential live vaccines for HIV, Vaccine. 2001, vol. 19, pp. 735-742, entire document.

Kingsman, A.J. et al. Yeast retrotransposon particles as antigen delivery systems. Ann. NY Acad. Sci. May 31, 1995, vol. 754, pp. 202-213 (abstract only).

Aiken, C.et al., "Inside-out Regulation of HIV-1 Particle Fusion", 10th Conf. on Retrovirus and Opportunistic Infections. Feb. 10-14, 2003, Boston, MA, Abstract 17.

Aroeti, B., et al.,"Mutational and Secondary Structural Analysis of the Basolateral Sortin Signal of the Polymetic Immunoglobulin Receptor", J. Cell Biology, 1993. vol. 123, No. 5, pp. 1149-1160.

Ara, Yuki, et al., "Zymozan enhances the immune response to DNA vaccine for human immunodeficiency virus type-1 through the activation of complement system", Immunology, 2001 vol. 103: 98-105.

Aslam, Mohammed, et al., "Folded Back Solution Structure of Monomeric Factor H of human Complement by Synchrotron X-ray and Neutron Scattering, Analytical Ultracentrifucation and Constrained Molecular Modeling", Molecular Biology, 2001, vol. 309: 1117-1138.

Ault, Bettina, et al., "Human FactorH Deficiency", Biology Chemistry, 1997, vol. 272, No. 40, pp. 25168-25175.

Blackmore, T.K. et al., "Identification of a Heparin Binding Domain in the Seventh Short Consensus Repeat of Complement FactorH", Immunology, 1996, vol. 157, Iss. 12, pp. 5422-5427.

Braaten, D. et al., "Cyclophilin A Regulates HIV-1 Infectivity, as demostrated by gene targeting of human T-cells", The EMBO Journal, 2001, vol. 20, No. 6, pp. 1300-1309.

Berger, R. et al., "Activation of the alternate pathway of complement: efficient fluid-phase amplification by blockade of the regulatory complement protien B1H through sulfated polyanions", European J. Immunology, 1981, vol. 11, pp. 291-293.

Doeppler, Susi, et al.,"Complement Receptors to HIV Infection", Current Molecular Medicine, 2002, vol. 2 Iss. 8, pp. 703-711.

Burger, R. et al., "Dextran Sulfate: A Synthetic Activator of C3 via the Alternative Pathway", Immunology, 1975, vol. 29, pp. 549-554.

Burger. R., et al.,"Insoluble polyanions as activators of both pathways of complement", Immunology, 1977, vol. 33, pp. 827-837.

Brooks. Geo F., Medical Microbioloy Ch 3 & 7(23rd Ed. 2004).

Burger, R., et al., "Activation of the alternative pathway of complement: eeficient fluid-phase amplification by blockade of the regulatory complement protein B1H through sulfated polyanions," European J. Immunology, vol. 11, pp. 291-293 (1981).

Friese, M.A., "FHL-1/reconectin and factor H: two human complement regulators which are encoded by the same gene are differently expressed and regulated," Molecular Immounology, vol. 36, pp. 809-818 (1999).

Furie, Bruce, "Oral Anticoagulant Therapy", Hematology Basic Principles & Practice, Ch. 121, pp. 2040-2046.

Gardner, William D., "Identificatin of a major human serum DNA-binding protein as B1H of the alternative pathway of complement activation", Biochemical and biophysical Research Communications, vol. 94, pp. 61-67 (1980).

Gasque, P., "Expression of complement components of the alternative pathway by glioma cell lines", Immunology, 149:1381-87 (1992).

Giannakis, Eleni, et al., "Multiple ligand binding sites on domain seven of human complement factor H", Int'l. Immunopharmacology, vol. 1, Issue 3, pp. 433-443 (2001).

Goudsmit, J. Immunodominant B-Cell epitopes of the HIV-1 enevelope recognized by infected and immunized hosts, AIDS, vol. 2 (Suppl 1); S41-S45 (1988).

Gowda, D.C., et al., "Immunoreactivity and Function of Oligosaccharides in Cobra Venom Factor", J. of Immun., vol. 152, Issue 6, pp. 2977-2986 (Dec. 1993).

Harrison, Stephen, Howard Hughes Medical Institute, Remarks for Institute News titled "HIV's Deep Picket May Reveal Vulnerability; Seeing the Structure of the Viral Protein gp41 suggested experimental design" (Sep. 28. 1999); Internet: www.hhmi.org/news.gp41.html.

Hurum, John, "Complement activation upon binding of mannam-binding protein to HIV emvelope glycoproteins", AIDS, vol. 7 (10), pp. 1307-1313 (1993).

Hellwage, J., "Functional Properties of complement factor H-related proteins FHR-3 and FHR-4: binding to the C3d region of C3b and differential regulation by Heparin", FEBS Lett. 426(3); 345-352 (Dec. 3, 1999).

Hoffman, Ronald, Hemotology Basic Principles and Practice, Ch. 36, pp. 640-651; pp. 651-667; Ch. 39, pp. 686-701 (3$^{rd}$ ed. 2000).

Hogan, Christine M. et al., "Host Determinants in HIV Invention and Disease", Ann. Intern. Med. 13(10); 978-996 (2001).

Hughson, F.M., "Enveloped viruses: A common mode of membrane fusion?" Current Biology 7(9): R565-R569 (1997).

Hughes, Huw, "Bacterial Vectors for Vaccine Delivery", Designer Vaccines: Principles for Successful Prophylaxis, Ch. 2, 8, pp. 151-178 (1998).

Joiner, K.A. "Complement Evasion by Bacteria and Parasites", Ann. Rev. Microbiol., vol. 42, pp. 201-230 (1988).

Johnston, Margaret, et al., "Progress in HIV vaccine development", Current Opinion in Pharmacology, 1:50-510 (2001).

Jokiranta, T., "Analysis of the recognition mechanism of the alternative pathway of complement by monoclonal anti-factor H antibodies: evidence for multiple interactions between H and surface bound C3b", FEBS Lett., 393:297-302 (Sep. 16, 1996).

Jokiranta, T., "Each of the Three Binding Sites on Complement Factor H interacts with a Distimct Site on C3b", J. of Biological chemistiy, vol. 275, #36, 27657-27662 (Sep. 8, 2000).

Kaplan, G., et al., "Construction and Characterization Poliovirus Subgenomic Replicons", J. Virol. 62(5):1687-96 (May 1988).

Kaufmann, Stefan H.E., Concepts in Vaccine Development, Ch. 2, 3, 7 (1996).

Keren, David F., et al.; "Combined Parenteral and Oral Immunization Results in an Enhanced Mucosal Immunoglobulin A Response to Shigella Flexen", Infect. Immun. 56:910-915 (1988).

Kirkitadze, Marina, et al.; "Structure and flexibility of the multiple domain proteins that regulate complement activation", Immun. Rev., vol. 180, pp. 146-161 (2001).

Kitamura, N. et al., "Primary structure, gene organization and polypeptide expression of poliovirus RNA", Nature 291: 547-553 (1981).

Kiyono, Hiroshi, et al., Mucosal Vaccines, Prospects for Induction of Mucosal Immunity by DNA Vaccines, Ch. 8, pp. 119, 127 (1996).

Kock, Michael A., et al., "Structure and function of recombinant Cobra Venom Factor", J. of Biol. Chemistry, vol. 279,pp. 30836-30843 (2004).

Lachmann, P.J., "The influence of C3b Inactivator (KAF) Concentration on the Ability of Serum to Support Complement Activation", Clin, Exp. Immonol., vol. 21, pp. 109-114 (1975).

Lee, Young-Min, et al., "A Bipartite Membrane-Binding Signal in the Human Immonodeficiency Virus Type 1 Matrix Protein is Required for the Proteolytic Processing of Gag Precursors in a Cell Type-Dependent Manner", J. of Virology, pp. 99061-9068 (Nov. 1998).

Legendre, C., et al., "Mechanisms of opsonized HIV entry in normal B lymphoytes", FEBS Lett. 381-227-232 (1996).

Levinson, Warren, et al., Medical Microbiology & Immunology, Chapter 58, pp. 363-381, 401(7$^{th}$ ed. 2002).

Levy, J.A., "Pathogenesis of Human Immunodeficiency Virus Infection", Microbiol. Rev 57(1): 183-289 (1993).

Lewis, P.J., et al. "Altering the Cellular Location of an Antigen Expressed by a DNA-Based Vaccine Modulates the Immune Response", Journal of Virology, 73(12); 10214-10223 (Dec. 1999).

Liang, J.F., et al., "A Less Toxic Haparin Antagonist-Low Molecular Weight Protamine", Biochemistry, vol. 68(1); 116-120 (2003).

Maillet, Francoise, et al., "Heparin Prevents Formation of the Human C3 Amplifaction Convertase by Inhibiting the Binding Site for B on C3b", Molecular Immun., vol. 20(12): 1401-1404 (1983).

Maillet, Francoise, et al., "Structure-function Relationships in the Inhibitory Effect of Heparin on Complement Activation; Independency of the Anti-coagulant and Anti-complementary sites on the Heparin Molecule", Molecular Immun., vol: 25(9): 917-923 (1988).

McRae, Jennifer, et al,; "Human Factor H-related Protein 5 (FHR-5)", Biological Chemistry, vol. 276 (9): 6747-6754 (2001).

MccMichael, Andrew, J., et al., "Cellular Immune responses to HIV", Nature, 410:980-987 (Apr. 19, 2001).

Meri, Seppo, et al.; "Discrimination between activators and nonactivators of the alternative pathway of complement; Regulation via a sialic acid/polyanion binding site on factor H", Proc. Natl. Acad. Sci., USA, vol. 87, pp. 3982-3986 (May 1990).

Michalek, Michael T., et al,, "Inhibition of the Alternative Pathway of Human Complement by Structural Analogues of Sialic Acid", J. Immunology, vol. 140, pp. 1588-1594 (1988).

Morrow, W. J., et al., "Circulating Immune Complexes in Patients with Acquired Immune Deficiency Syndrome Contain the AIDS-Associated Retrovirus", Clin. Immunol. and Immunopathol., 40:515-24 (1986).

Nicholl, Desmond, An Introduction to Genetic Engineering, Ch. 3, 5 (2nd Ed. 2002).

Nilsson, U.R., et al., J. Exp. Med. 122: 277-289 (1965).

Ono, Akira, et al., "Binding of Human Immunodeficiency Virus Type 1 Gag to Membrane: Role of the Matrix Amino Terminus", J. of Virology, vol. 73, No.5, pp. 4136-4144 (May 1999).

Pangburn M.K., "Analysis of Recognition in the Alternative Pathway of Complement: Effect of Polysaccharide Size", J. of Immunol, vol. 142 (8), 2766-2770 (Apr. 1989).

Pangburn, M.K., "Molecular Mechanisms of Target Recognition in an Ionate Immune System: Interactions Among Factor H, C3b, and Target in the Alternative Pathaway of human Complements: effects of Polysaccharide Size", J. of Immunol., vol. 164; pp. 4742-4751 (2000).

Pantaleo, G., et al., "Studies in Subjects With Long-Term Nonprogressive Human Immunodeficiency Virus Infection", N. Engl. J. Med. vol. 332, No. 4, 332:209-16 (1995).

Parham, Peter, The Immune System, Ch. 7. 12 ($2^{nd}$ Ed. 2004).

Paul William E.; Fundamental Immunology, pp. 967-994 ($4^{th}$ ed. 1999).

Pinter, Claudia, et al., "HIV Glycoprotein 41 and Complement Factor H Interact with Each other and Share Functional as Well as Antigenic Homology", AIDS Research in Human Retroviruses, vol. 11(8): 971-80 (Nov. 8, 1995).

Pinter, Claudia, et al., Direct Interaction of Complement Factor H Interact with the C1 Domain of HIV Type 1 Glycoprotain AIDS Research and Human Retroviruses; vol. 11(5): 577-588 (Nov. 8, 1995).

Porter, Donna C., et al., Encapsidation of Poliovirus Replicons Encoding the Complete Human Immunodeficiency Virus type gag Gene by Using a Complementation System Which Provides the P1 Capsid Protein in trans, Journal of Virology, vol. 69(3); 1548-1555 (March 1995).

Presanis, J.S., et al., "Biochemistry and genetics of mannan-binding lectin (MBL)", Biochemical Society Transactions, vol. 31, Part 4, pp. 748-752 (2003).

Procaccia, S. et al., "Rheumatoid factors and circulating immune complexes in HIV infected individuals", AIDS, vol. 5(12): 1441 (1991).

Racaniello, V.R., et al., "Molecular cloning of poliovirus cDNA and determination of the complete nucleotide sequence of the viral genome", Proceedings of the National Academy of Sciences, USA, 78(8); 4887-4891; (Aug. 1981).

Reisenger, E.C., et al., "Complement-mediated enhancement of HIV-1 infection of the monoblastoid cell line U9317", AIDS, vol. 4, pp. 961-965 (1990).

Ren, R., et al., "Human Poliovirus Receptor Gene Expression and Poliovirus Tissue Tropism in Transgenic Mice", J. of Virol. 66(1); 269-304 (1992).

Resh, Marilyn D., "A myristoyl switch regulates membrane binding of HIV-1 Gag"; Proc. Natl. Acad. Sci., vol. 101(2), 417-418 (Jan. 13, 2004).

Ripoche, Jean et al., "The complete amino acid sequence of human complement factor H", Bichem J., vol. 249, pp. 593-602 (1988).

Robinson, Jr. W.E., et al., "Antibody-Dependent Enhancement of Human Immunodeficiency Virus Type 1 Infection", The Lancet, pp. 790-794 (Apr. 1988).

Sahu, Arvind, et al., "Specificity of the thioester-containing reactive site of human C3 and its significance to complement activation", Biochem J., vol. 302, pp. 429-436 (1994).

Sande, Merle A, et al., The Medical Manigement of AIDS ($6^{th}$ ed. 1999).

Saphire Andrew C.S., et al., "Host cyclophilin A mediates HIV-1 attachment to target cells via heparans", The EMBO Journal, vol. 18, #23, pp. 6771-6785 (1998).

Sherry, Barbara, et al., "Role of cyclophilin A in the uptake of HIV-1 by macrophages and T lymphocytes"; Proc. Natl. Acad. Sci., vol. 95, pp. 1758-1763 (1988).

Skerka, C., et al., "Mapping of the Complement Regulatory Domains in the Human Factor H-like Protein I and in Factor H" J. of Immune, 155(12): 5663-5670 (Dec. 1993).

Smith, Colleen, Basic Medical Biochemistry: A Clinical Approach, Ch. 17 (2d. ed. 1996).

Spear, G.T., et al. "Human immunodeficiency virus (HIV)-infected cells and free virus directly activate the classical complement pathway in rabbit, mouse and guinea-pig sera; activation results in virus neutralization by virolysis", J. of Immunology, vol. 73, pp. 377-382 (1991).

Speth, C., et al., "Complement receptors in HIV infection", Immunological Reviews, vol. 159, pp. 49-67 (1997).

Speth, C., et al., "The complement system: Pathophysiology and clinical revelance", The Middle European J. of Medicine, 111/10; 378-391 (1999).

Stahl, Stefan, et al., "Strategies for Gene Fuson", Methods in Molecular Biology, 62: 37-54 (1997).

Stoiber, Herbert et al., "The envelope glycoprotein of HIV-1 gp120 and human complement protein C1q bind to the same peptides derived from three different regions of gp41, the transmembrane glycoprotein of HIV-1, and share antigenic homology", European J. of Immun., vol. 24, pp. 294-300 (1994).

Stoiber, Herbert et al., "Human Complement Proteins C3b, C4b, Factor H and Properdin React with Specific Sites in gp120 and gp41, the Envelope Proteins of HIV-1"; Immunobiology, vol. 193, pp. 98-113 (1995).

Stoiber, Herbert et al., "Efficient Destruction of Human Immunodeficiency virus in Human Serum by Inhibiting the Protective Action of Complement factor H and Decay Accelerating Factor (DAF, CD55)", J. Exp. Med., vol. 183, pp. 307-310 (Jan. 1996).

Stoiber, Herbert et al., "The Role of Complement in HIV Infection", Annu. Rev. Immunol., 15:649-674 (1997).

Stoiber, Herbert et al., "Role of Complement in the control of HIV dynamics and pathogens", Vaccine, 21: S2/77-S2/82 (2003).

Sun, J., Neuraminidase from a Bacterial Source Enhances Both HIV-1 Mediated Syntium formation and the virus Binding/Entry Process; Virol. 2001; Abstract 0340837 A1 (Merk & Co. Inc.); Nov. 8, 1989; p. 4, lines 17-30, p. 5, lines 15-16.

Sun, Jiangfeng et al., "Syncytium Formation and HIV-1 Replication are both Accentuated by Purified Influenza and Virus-associated Neuraminidase", J. of Biol. Chemistry, 277 (12); 9825-9833 (2002).

Tang, Chung et al., "Entropic switch regulates myristate exposure in the HIV-1 matrix protein", Proc. Nat'l Acad. Of Sci., 101(2); 517-522 (Jan. 2004).

Thali, M. et al., "Functional association of cyclophilin A with HIV-1 virions", Nature, 372, (6504): 363-5 (1994).

Thieblemont, N., et al, Triggering of Complement Receptors CR1 (CD35) and CR3 (CD11b/CD18) Induces Nuclear Transiocation of NF-KB (p50/p65) in Human Monocytes and Enhances Viral Replication in HIV-infected Monocytic Cells, J. of Immunology, vol. 155, p. 4861-4867 (1995).

U.S. Environmental Protection Agencey, Health Assesment Document for Nickel; EPA/600/8-83/012F; National Center for Environmental Assesment, Office of Research and Development, Washington, DC, 1986.

Vajdos, Felix, et al., "Crystal structure of cyclophilin A complexed with a binding size peptide from the HIV-1 capsid p"; Protein Science 6 (11); 2297-2307 (1997).

Vogel, Carl W., "Antibody Conjugates without Inherent Toxicitiy; The Targeting of Cobra Venom Factor and Other Biological Response Modifiers"; Immunoconuugates, Ch. 9; pp. 170-188 (1987).

Wagner, Edward K., Basic Virology, pp. 105-108, 368 (1999).

Walker, Christopher, et al., "Catholic lipids direct a viral glycoprotein into the Class 1 major histocompatibility complex antigen-presentation pathway", Proc. Natl. Acad. Sci., 89: 7915-1918 (Sep. 1992).

Weiler, John M., et al., "Modulation of the formation of the amplification convertase of complement, C3b, Bb, by native and commercial Heparin"; J. Exp. Med. vol. 147, pp. 409-421 (1978).

Weissenhorn, W., et al., "Atomic structure of the ectodomain from HIV-1 gp41", Nature, vol. 387. pp. 426-630 (May 1997).

Winkelstein, J.A., et al., "Activation of the Alternative Complement Pathway by Pneumococcal Cell Wall Teichoic Acid", J. of Immun. vol. 120, pp. 1678-178 (1978).

Zipfel, P.F., et al.; "Complement factor H and related proteins: an expanding family of complement-regulatory protiens?" Immunology Today, 15(3): 121-126 (1994).

METHODS OF INDUCING TH-1 IMMUNE RESPONSES TO HIV-1 BY ADMINISTERING UV/PSORALEN-TREATED DESIALATED INACTIVIATED HIV-1 VIRIONS DEFICIENT IN CD55 AND CD59

CROSS REFERENCE TO RELATED APPLICATIONS

The present application is a Continuation-in-part application that claims priority to U.S. Provisional Application Ser. No. 61/195,541 filed Oct. 8, 2008 and the related U.S. Non-Provisional application Ser. No. 10/971,426 filed Oct. 22, 2004 which claims priority to U.S. Provisional Application Ser. No. 60/513,827 filed Oct. 23, 2003; U.S. Provisional Application Ser. No. 61/195,540 filed Oct. 8, 2008 and the related U.S. Non-Provisional application Ser. No. 12/315,776 filed Dec. 5, 2008 which is a Divisional Application of U.S. Non-Provisional application Ser. No. 10/971,445 filed Oct. 22, 2004 which claims priority to U.S. Provisional Application Ser. No. 60/513,827 filed Oct. 23, 2003; U.S. Provisional Application Ser. No. 61/195,539 filed Oct. 8, 2008 and the related U.S. Non-Provisional application Ser. No. 12/229,863 filed Aug. 27, 2008 which is a Continuation Application of U.S. Non-Provisional application Ser. No. 10/971,229 filed Oct. 22, 2004 which claims priority to U.S. Provisional Application Ser. No. 60/513,827 filed Oct. 23, 2003; and U.S. Provisional Application Ser. No. 61/111,526 filed Nov. 5, 2008; which are hereby incorporated in their entirety by reference.

FIELD OF THE INVENTION

This invention relates to the field of virology and immunology. An aspect of the invention relates to methods of administration of an immunogenic composition based on an HIV fusion protein, and HIV matrix protein, or psoralen inactivated HIV.

BACKGROUND OF THE INVENTION

Despite profound efforts, there is no curative vaccine for HIV. Various steps of the HIV life cycle have been targeted by inventors. To date, research has not found a composition that will foster an effective immune response against the immunosuppressive retrovirus HIV-1. As disclosed in related U.S. patent application Ser. No. 10/971,426, HIV fusion protein serves as a basis of an immunogenic composition against HIV. As disclosed in related U.S. patent application Ser. No. 10/971,229 HIV an HIV-1 matrix protein serves as a basis of an immunogenic composition against HIV. As disclosed in related U.S. patent application Ser. No. 10/971,445, psoralen inactivated HIV serves as a basis of an immunogenic composition against HIV. An embodiment of the present invention further contemplates specific administration protocols for the HIV fusion protein, matrix protein and psoralen inactivated HIV based immunogenic compositions.

SUMMARY OF INVENTION

An aspect of the invention relates to methods of administration of an immunogenic composition based on an HIV fusion protein, matrix protein and psoralen inactivated HIV. The immunogenic compositions are based on HIV biologically active fusion peptide, matrix peptide, or psoralen inactivated HIV. The number of doses is 3X. The starting dose for an adult is $1 \times 10^9$-$1 \times 10^{10}$. The starting dose for an adolescent is ½ ($1 \times 10^9$-$1 \times 10^{10}$). The starting dose for a pediatric patient is ¼ ($1 \times 10^9$-$1 \times 10^{10}$). The second dose will consist of $\frac{1}{10}^{th}$ of starting concentrations. The third dose will consist of $\frac{1}{100}^{th}$ of starting concentrations. This will facilitate a Th-1 response. The days of administration are days 1; 30; and 180. Alternatively the days of administration are days 1; 20-40; and 160-200. The site of administration is one that targets lymphatic tissue. Adjuvant is administered before, simultaneous with or after each dose of the immunogenic compositions. Adjuvants are used to promote a Th-1 immune response and include a leukotriene receptor antagonist such as Montelukast, a mast cell and basophil stabilizer such as Cromolyn, and a prostaglandin synthetase inhibitor such as Indomethacin. Th-1 immune responses to the immunogenic compositions are monitored. The 3X cycle will repeat on until a Th-1 immune response is observed. At that point, the immunogenic composition administered could then decline by a factor of 10 for two more vaccination procedures.

DESCRIPTION OF THE INVENTION

Figure 1:
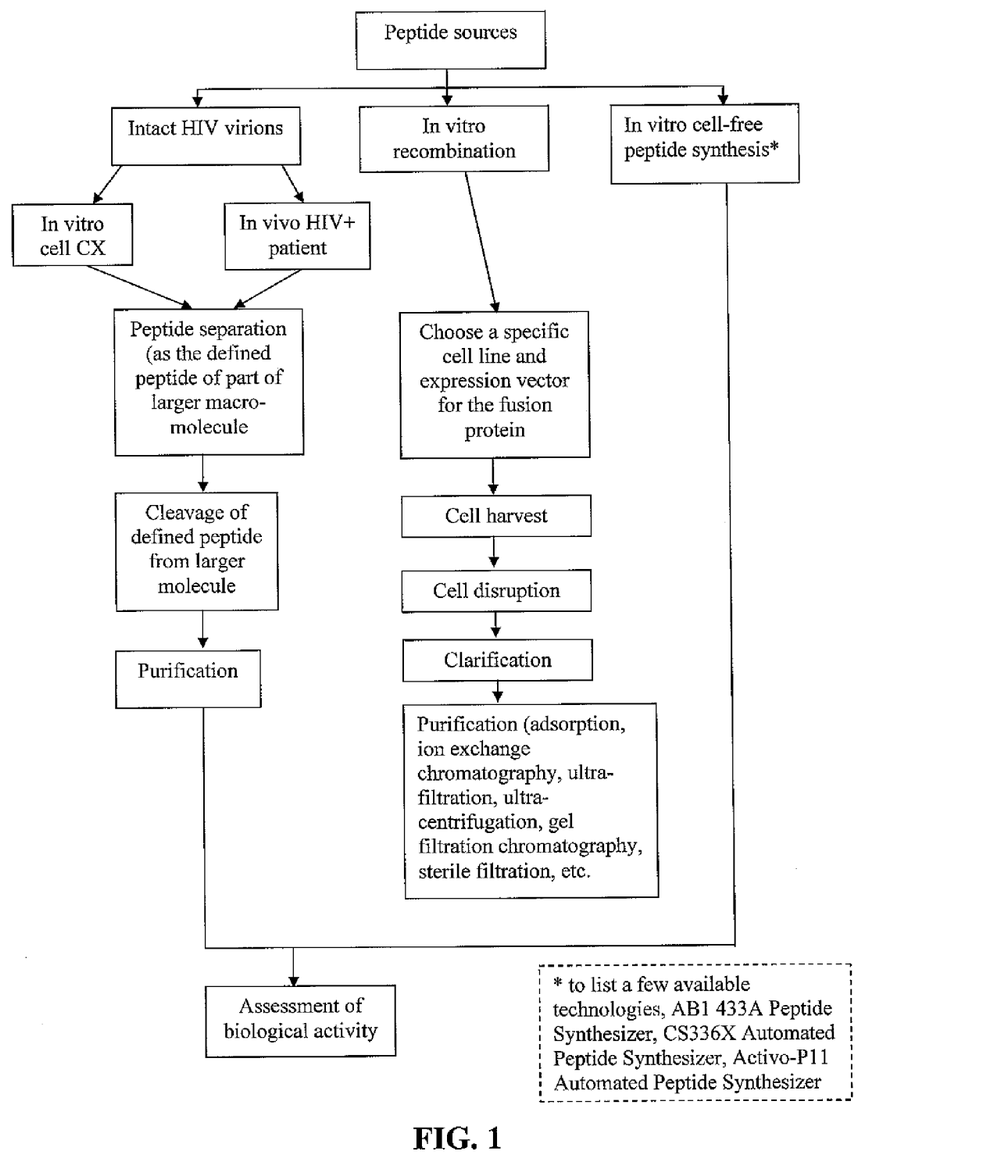
FIG. 1 is a flowchart for fusion protein and matrix protein synthesis, purification, and assessment of biological activity.
Figure 2:
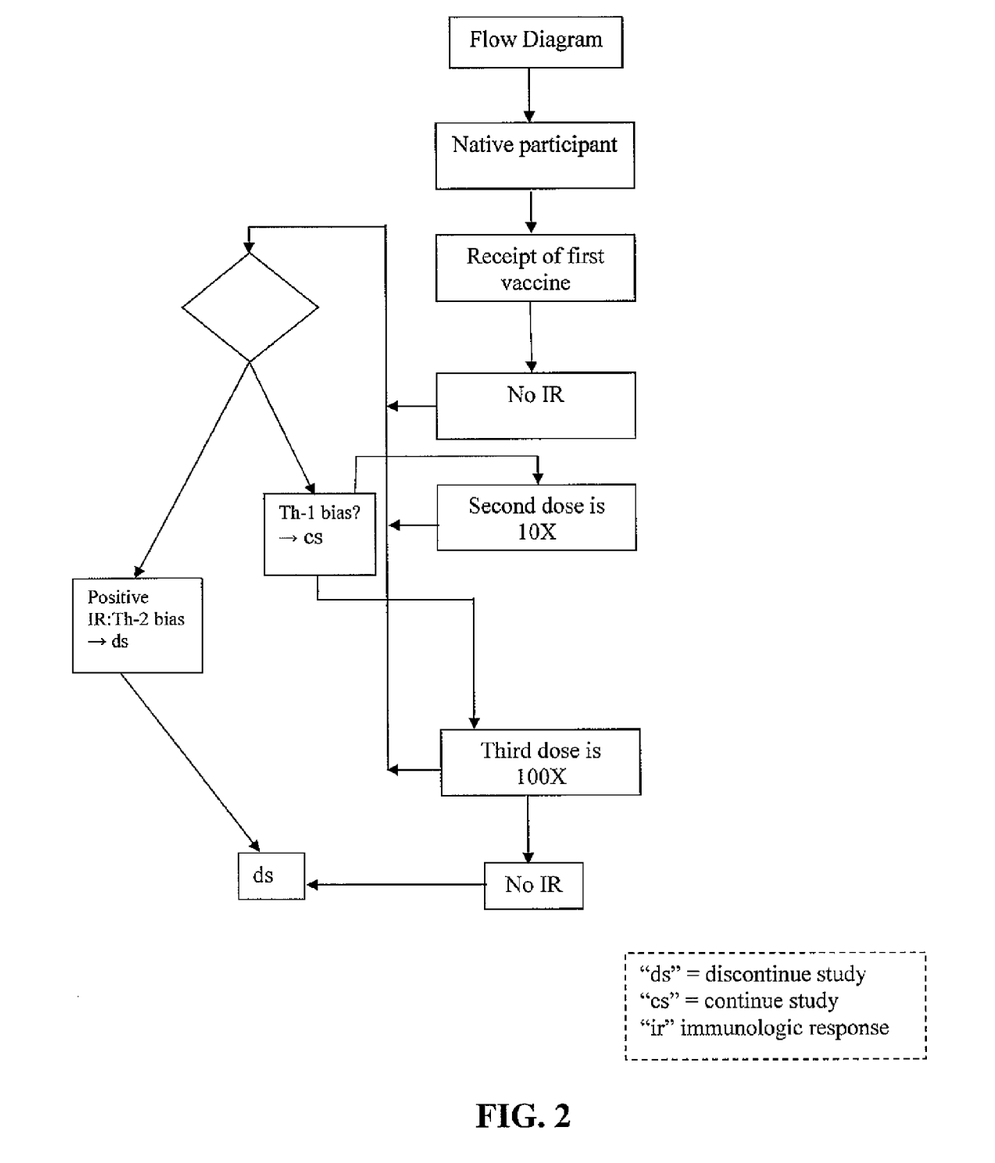
FIG. 2 is a flowchart of an administration and dosing regimen of an immunogenic composition based on HIV fusion protein, matrix protein or psoralen inactivated HIV.

The smallest amount of antigen that elicits an immune response is most likely to facilitate a Th-1 response. The minimal amount of antigen administered can be a starting point for all vaccine recipients. Ideally, all would have no response to the initial dose. Subsequent vaccinations would consist of a ten-fold increase in biologically active antigen. This would continue on until an immune response is noted in follow-up laboratory procedures. At that point, the vaccine administered would then decline by a factor of 10 for two more vaccination procedures.

In one embodiment, the dose of antigen required to elicit the initial response may be the same, or close to the same, for all participants. In another embodiment, the dose of antigen required to elicit the initial response may be different for participants. In another embodiment, variations of this procedural protocol may be streamlined and/or altered by those of ordinary skill in the art for this type as well as follow-up studies.

Sample Protocol I:

Cloning the DNA Encoding the Fusion Protein and Matrix Protein

A variety of DNA technologies allowing the investigator to construct and replicate recombinant DNA molecules after transfer of the recombinant nucleic acid into a host cell, prokaryotic or eukaryotic have been defined in the literature. Characteristically, the bacterium *E. coli* also known as K12 has been the defining gold standard for prokaryotic recombinatory DNA vector systems. Yeast such as *Saccharomyces cerevisiae* has been utilized as a host cell for the cloning as well as the expression of viral and eukaryotic genes. Yeast artificial chromosomes have been developed which are able to clone fairly large sizes of DNA. Gene transfer into plant cells can be accomplished by bacterial plasmid vectors. The bacterium *Agrobacterium tumifaciens* for gene transfer into plants is also well defined. Viral DNA can also be transferred into mammalian cells in vitro which can be used as a source for clone DNA. Methods of DNA transfer include endocytosis, liposomes, plasmids and gene gun technology. Retroviral vectors have also been utilized to insert foreign DNA into a targeted host mammalian cell. PCR will allow in vitro amplification of any defined DNA segment.

The intact HIV virion or defined structural protein derived from the HIV virion can be a source of the fusion protein and matrix protein. The HIV virion can be derived from an HIV positive patient or an in vitro cell culture or other procedures known in the art.

Assessment of Biological Activity of the Fusion Protein

The fusion protein mediates the fusion of the viral and targeted cell plasma membrane. Disruption of the targeted cell membrane can be noted by changes in the UV absorption spectrum of the targeted plasma membrane. The molecular weight of the fusion protein has been defined. Therefore, the number of individual fusion proteins can be determined by measuring the weight of the targeted immunogen. Total weight of the targeted immunogen divided by the molecular weight of the fusion protein will yield the number of individual fusion proteins (X).

The number of cells (Y) in a target medium can also be accurately estimated by a variety of technologies currently available to the cell physiologist. Monoclonal antibodies to the fusion protein can be produced or are available commercially. A specified number of fusion peptides (X) can be added to a cell culture consisting of (Y) number of viable cells. The number of cells and/or percentage of cells with a disrupted plasma membrane can be documented by changes in UV absorption of the plasma membrane.

As a control, fusion peptides bound to monoclonal antibodies will be added to an identical cell culture. The control should demonstrate minimally, if any, plasma membrane disruption. The test vehicle containing fusion peptides unbound to monoclonal antibodies will yield a certain number or percentage of penetrated/disrupted plasma membranes. The number or percent of plasma membranes disrupted by the control should be subtracted from the actual test vehicle (if the control is done appropriately, this number will approach zero). This will give a reproducible, standard, biological assay of fusion protein function which can be given a specific value. Using the standardized cell culture, the biological activity of a fusion protein derived from any source can be determined and quantified.

In a cell culture of Y number of cells in which a specified number of fusion peptides (X) has been added, a number of cells (A) will have a disrupted plasma membrane and a number of cells (B) will have an intact plasma membrane. $Y=A+B$.

After addition of the fusion peptide, a number of ratios can be used to assess biological activity. In one embodiment, the ratio is A/Y. Other ratios such as B/Y or A/B or B/A can also be used.

In one embodiment, the A/Y ratio employed as a measure of biological activity may be 0.5 or greater. This ratio will allow for accurate assessment of the functional immunogenicity of the compound at its time of manufacture. Stability of the product can also be assessed periodically and just prior to administration.

Assessment of Biological Activity of the Matrix Protein

The matrix protein must undergo N terminal myristoylation on the N terminal glycine residue. The enzyme accomplishing this, N-myristoyl transferase (NMT) is a monomeric enzyme catalyzing transfer of myristate from myristoyl-CoA to a targeted peptide.

The matrix protein and its molecular weight have been defined. The weight of a pure composition of matrix protein can be determined. Divided by the molecular weight of the matrix protein, the number of matrix peptides can be determined.

Biological activity of the matrix protein will be dependent upon its ability to undergo N terminal myristoylation and its subsequent ability to attach to a targeted cell plasma membrane.

A defined quantity of unprocessed matrix proteins (X) can undergo N terminal myristoylation with a defined number of NMT enzymes (Y) to yield the matrix protein with an N terminal myristoyl moiety. Differences in the sedimentation coefficients of the myristoylated matrix protein (A) and the non-myristoylated protein (B) will allow easy separation of the two molecules. The molecular weight of the myristoylated matrix protein has been determined and this will facilitate quantification of the number of matrix proteins (A) that were bound to myristate by NMT at the N terminal glycine residue and the number of matrix proteins that were not bound to myristate (B). $X=A+B$.

The first measure of biological activity is the capacity of the immunogen to covalently bond myristate. Multiple ratios can be used. In one embodiment A/X is used. Other ratios include B/X, A/B and B/A.

The myristoylated matrix proteins (A) are then added to an in vitro erythrocyte cell culture. Erythrocytes do not have a nucleus and therefore are not capable of replication and have a long half life of approximately ninety days. An accurate estimate of the number of erythrocytes (C) in a cell culture can be defined by a cell physiologist by a number of technologies currently employed. This number will stay constant over the duration of this procedure since the time sequence of this procedure will be measured in minutes or hours, not days or weeks. After a short incubation period (in one embodiment—approximately thirty minutes) the red blood cells will be separated from the unbound myristoylated matrix proteins (D) by centrifugation. The total number of myristoylated matrix proteins (A) equals the number of bound (E) and unbound myristoylated matrix proteins (D). Therefore $A=D+E$.

Numerous ratios can be utilized to assess this stage of biological activity. In one embodiment E/A is used. In one embodiment, the final calculation of biological activity will be $A/X \times E/A$.

A defined measure of biological activity will serve multiple functions. For example, before a vector can be considered a part of an immunogen composition, it must have the biological activity of at least 0.5. To assess stability of the immunogen, the biological activity can be reassessed at various times. Significant decline of more than 5% of the original number would result in elimination of that immunogen composition from use.

The fusion protein and matrix protein synthesis, purification, and assessment of biological activity are illustrated in FIG. 2 in a flowchart.

Sample Protocol II for Psoralen Inactivated HIV Based Immunogen

One aspect of the present invention is a composition capable of invoking an immune response, wherein certain predetermined strains of HIV relevant to the use of the composition are isolated and inactivated using psoralen and exposure to light, and further where features of HIV that impair immune response are removed from the inactivated HIV. The composition may further comprise a pharmacologically appropriate carrier, stabilizer, or excipient.

In an alternate embodiment intended for use as a vaccine for an infected animal, the vaccine may include those strains present in the animal at the time the sample was drawn, matching the genotype of the vaccine to that of the infection. Alternatively, a preventive vaccine may include strains of concern based on probability of exposure. The vaccine may be treated to remove features of the HIV that impair immune response.

Another aspect of the invention is a method of preparing an immunogenic composition comprising determining the strains of HIV relevant to the use of the composition, inactivating the strains using psoralen and exposure to light, and removing or modifying features of the HIV that impair immune response. In particular, these features or components may comprise the complement Factor H binding sites for gp160, gp120, and gp41, removal of sialic acid residues, and optionally the outer cellular plasma membrane. Therefore, a methodology of the present invention comprises for preparation of an immunogenic composition includes:

1. Determining the strains of HIV that are of concern
2. Isolating and culturing the strains of concern
3. Separating the virus from the culture media
4. Optionally removing the cellular outer plasma membrane
5. Adding psoralen and a DNA-repair enzyme blocking agent
6. Irradiating with ultraviolet light
7. Removing or neutralizing CD55 and CD59
8. Desialation of the inactivated virus The present invention is thus an immunogenic composition comprised of a tailored combination of psoralen inactivated HIV subtypes, and a method of preparing and using the same.

Determination of Relevant Strains

The determination of the strains of HIV will depend on the embodiment and application of the present invention. There are a wide variety of applications for immunogenic compositions; accordingly, the following should be construed as exemplary and not limiting. The determination of HIV strains that are relevant may be considered in three exemplary categories: (i) research related, development, analytical; (ii) therapeutic; and (iii) preventive.

In one category of embodiments, the immunogenic composition may be contemplated for use in research or clinical analysis. For research, the strains of concern will be determined by the objectives of the scientific investigation. That is, the procurement, isolation, and culture of the HIV virus will accord with the investigatory design and objectives. The determination of relevant strains for medical research may likely parallel that for any envisaged therapeutic or preventive need, such as vaccine development. Purely academic research may encompass aspects such as the development of research tools or expanding knowledge about strains unrelated to the HIV epidemic. The immunogenic composition may also be useful in studies of immune response, viral evolution, epidemiology, and analysis of viral behavior.

In another category of embodiments, the immunogenic composition may be intended for administration to an HIV infected human (or other animal or host), possibly as a therapeutic vaccine. In general, multivalent immunogenic compositions should have the ability to induce an immune response against diverse viral isolates; in the past, this multivalence would involve a combination of inactivated viral particles from a variety of strains of concern. However, HIV within an individual host is rarely static, and continues to evolve through genetic mutation and recombination. Past efforts to target common strains or variants in a multivalent HIV vaccine rely on macroscopic public health predictors and conservative over sampling of HIV strains. In the present invention, the strains of HIV may be genotyped and isolated from a sample drawn from the infected human or other animal. That is, peripheral blood mononuclear cells (PBMC) or other sample may be drawn in order to identify the HIV present in the infected human or other animal. Any typing method appropriate to the circumstances may be used, including sequence based diagnostic genotyping, heteroduplex mobility assay (HMA), analyte specific reagents assay genotyping, molecular diagnostics, gene detection products, and DNA probe-based products. A vaccine may then be composed of those strains present in the human at the time the sample was drawn. Thus, in one embodiment, the HIV in a human (or animal model) is genotyped and the information is used to create a composite vaccine composed of stock components derived from inactivated virus for each of the identified strains. As described below, this alternative may involve a vaccine derived from virus cultured from human PBMCs in vitro or other sample drawn from a person (or other animal) that then undergoes the process of psoralen inactivation before being re-introduced into that person or other animal as an immunogen. In this way, the immunotherapy is tailored to the genotype of that host's virus. The methodology of the present invention contemplates a plurality of samples to identify and address changes in strain dominance or composition over time and, in response, enable changes in treatment. When a dominant strain is destroyed, a distinct but related resistant variant may then emerge, requiring further immunotherapy.

In another category of embodiments, the immunogenic composition may be contemplated for administration to an uninfected human, possibly as a preventive vaccine. In the past, the preventive composition and administration have been similar to that used in therapeutic multivalent compositions; such compositions may be based on the combined use of viral particles from a wide variety of strains intended to induce a broad immune response. Such an approach is contemplated as one embodiment of the present invention in preventive form.

Alternatively, the present invention in a preventive embodiment may also be based on a probabilistic assessment of the risk of exposure for that person. Notably, U.S. Pat. No. 6,503,753 contemplated personal preventive vaccines in cases where the risk of transmission was primarily through a particular individual; accordingly, the inactivated strains may be derived from a sample drawn from that infected individual. Such personal vaccines could be used as an embodiment of the present invention. Likewise, laboratory workers or healthcare professionals may face heightened risk from occupational exposure to certain known strains and may benefit from improved immune response to those specific strains. Alternatively, strain determination for personal vaccines may be based on behavioral and demographic risk factors for HIV infection in geographic areas of concern. Such analysis could consider behavioral patterns in the context of historic, epidemic, and geographic data supporting an exposure probability analysis. In geographic areas where the epidemic has spread beyond groups with identifiable risk factors, then multivalent prevention could reflect all known strains by geographic area of concern.

Procurement and Preparation for Irradiation

The following embodiments are to be considered exemplary and not limiting, as there are well established methods for procurement, isolation and culturing viruses. In fact, the actual virus may be procured in a variety of ways. Individuals infected with the HIV strains may be sampled and the virus may be isolated, purified, cultured, and typed using procedures that are known in the art, and are in part discussed below. Such samples may be drawn from PBMC or other fluids, such as saliva, or tissues, such as relevant mucous membranes; however, as is known in the art, PBMC may be preferable for its inclusion of immune components, depending on the application. Alternatively, HIV may be procured from existing samples of known commercial viral stocks or laboratory isolates. Viral particles may also be produced by transformation of cells with viral-encoding vectors, which is the uptake of foreign genetic material into a cell. Transformation is usually accomplished by physical means such as co-precipitation of the DNA with insoluble calcium chloride. (Nicholls, Desmond, An Introduction of Genetic Engineering (2nd ed. February 2002)) Transformed DNA can either exist in the cell as an episomal (extra chromosomal) element or be integrated within the nuclear genome. The efficiency of a DNA transfer into cells depends on the particular method used. The descriptions below may be common to the various categories of embodiments herein, unless otherwise specified.

The present invention contemplates various preferable culture media. A first preferable culture media is the PBMC drawn from an HIV infected host. In this embodiment, the HIV cells would replicate within the preserved in vitro host environment. Such a media may be safer and simpler for subsequent administration to the host. However, many culture media such as human cells or yeast include DNA-repair enzymes that can reverse the effect of psoralen. These enzymes can repair DNA and RNA through transcription coupled repair and global genomic repair. Thus, culturing in PBMC or yeast cells would be improved by inhibition of any enzymes that would tend to repair the DNA and RNA following exposure to psoralen and ultraviolet light. In a preferred embodiment, such media may be treated with repair enzyme inhibitors such as novobiocin, aphidicolin, or both. (Brenneisen, Peter, et. al., J. of Biological Chemistry, Vol. 275(6), pp. 4336-44 (Feb. 11, 2000)) (Niggli, H. J., Mutation Research, Vol. 295(3), pp. 125-33 (August 1993)) (Cleaver, J. E., J. of Cancer Research, Vol. 47(9), pp. 2393-6 (May 1987)) (Rosentein, B. S., et al., Environmental Mutagenis, Vol. 8(3), pp. 335-43 (1986)) In another preferred embodiment, the culture media is any media lacking or having low levels of such DNA-repair enzymes, such as Fanconi anemia type C. Fanconi anemia type C has a deficiency of DNA-repair enzymes, reducing recombination and making it preferable for use with psoralen inactivation. Some mutant cultures are known to be defective in excision repair of UV-induced pyrimidine dimers and are hypersensitive to photo addition of both mono and bi-functional psoralens. Examples are uvrA, B, or C mutants of *Escherichia coli*, of RAD3 type units of *Saccharomyces cerivisiae*, Chinese hamster ovary cancer cells complementation groups 1 and 4, Xeroderma pigmentosum groups A and D. Other culture media may be functionally equivalent so long as the operation of UV light damage DNA-repair enzymes is inhibited.

For an HIV negative human (or animal) a suitable vaccine/immunogen can be produced by culturing the virus in vitro before psoralen inactivation. Many culture media are available but a preferred embodiment would be a human's own peripheral blood mononuclear cells (PBMCs). This would subject the virus to a selective pressure generated by the human's own immune system. The strain(s) of HIV that replicate in vitro in such a culture would be the strains the human would most likely replicate in vivo in producing an active infection. Therefore each HIV negative and HIV positive human could have a tailored made vaccine.

Separation of the virus from culture cells may be accomplished by centrifuging the cells for ten minutes at 2000 rpm and at 4° C. The supernatants may then be filtered twice through a 0.22 millimicron Millipore filter.

In some cases, it may be desirable to remove host cellular outer membrane or membrane particles that could impede access to the viral components. In that case, disruption or removal of the outer membrane can be accomplished by means that are known in the art, such as treatment with ethanol, detergents, phenols, or other solvents. Importantly, removal of the outer membrane should not otherwise alter the viral structure or denature any viral proteins. (Levinson, Warren, Medical Microbiology & Immunology: Examination and Board Review (7th ed. July 2002)) In a first embodiment, such removal may be accomplished by detergents; detergents are "surface-active" agents composed of a long-chain lipid soluble hydrophobic portion and a polar hydrophilic group. The hydrophilic group may be a cation, an amine, a non-ionic group or multivalent. Surfactants interact with the lipid in the cell outer membrane through their hydrophobic chain and with the surrounding water through their polar group and thereby disorganizes the outer membrane. Quaternary ammonium compounds, such as benzalkonium chloride are cation detergents widely used for skin antisepsis and would be preferable for application here. Alternatively, ethanol will disorganize the lipid structure in the outer membrane; uncontrolled, it could denature proteins—which may be a limiting factor. Ethanol is more effective when diluted with water, for example, 70 percent ethanol is preferable to 100 percent. Thirdly, phenols such as hexachlorophene or cresol may be appropriate in some embodiments. The use of any of these substances should be under conditions that preserve the antigenic nature of the inactivated virus, preserves the viral structure, and avoids denaturing of the viral proteins.

The inactivation agent is preferably psoralen, as it is able to preserve the antigenic properties of the viral structure while inactivating RNA and DNA. Psoralens are a class of photomutagenic and photo-chemotherapeutic compounds that covalently modify nucleic acids. They belong to a family of small molecules that intercalate and photoalkylate DNA and RNA (both single stranded and double stranded.) The primary targets of psoralens are thymidine residues in DNA and uracil residues in RNA; these molecules form both monoadducts and interstrand cross links. The reaction takes place between the 3,4 (pyrone) or 4',5' (furan) double bonds of the psoralen and the 5,6 double bond in pyrimidines. The photobinding of psoralens to double strand DNA (dsDNA) results in substantial structural distortion of the normal DNA double helix. (Spikes, John D., Photosensitization in Mammalian Cells, Ch. 2 (1983)) (Averbeck, D., et al., Mutagenic Effects of Psoralen-Induced Photo adducts and Their Repair in Eukaryotic Cells, Pp. 933-59 (1988))

The immunogenic composition for one or more predetermined subtypes of HIV may be prepared for irradiation as follows. The HIV virions of concern in culture may be diluted in a solution containing 4'-aminomethyl4,5',8-trimethylpsoralen (AMT). Psoralen derivatives readily pass through cell walls and through virus coats and can then photoreact after exposure to UV light with the nucleic acids inside, producing pyrimidine dimers. AMT cross-links the viral RNA and DNA. All psoralens are photoactive.

Irradiation

Upon exposure to UV light, the psoralens form photoadducts with nucleic acids. This process does not require oxygen, and preferably oxygen should be removed. Psoralens can be irradiated before the addition of nucleic acids and photoadducts will still result. The HIV virus can then be inactivated with AMT and UV light. The virus is then unable to replicate its nucleic acid because the cross-linked DNA or RNA cannot be copied. The virus is thereby "killed" by inactivation of its DNA or RNA. Because photoreaction blocks the replication and expression of nucleic acid, it forms the basis of a technique for eliminating the infectivity and virulence of viruses. The surface of the virus remains largely unmodified, rendering the inactivated virus potentially useful for vaccines.

Psoralen photo-inactivation has proved to be superior to conventional inactivation techniques, such as formaldehyde treatment, for the preservation of antigenicity and immunogenicity in experimental inactivated vaccines. (Hanson (1992)) Photoreaction with AMT has been shown to remove the HIV infectivity from HIV-infected cells without altering antigenic surface properties; these inactivated cells retain normal reactivity with monoclonal antibodies to a variety of both cellular and viral antigens. (Hanson, 1992)

In HIV infected cell cultures, numerous DNA transcripts of the viral genome are produced in the infected cell and may eventually spill from lysing cells into the culture medium. While it is not known if such DNA or RNA poses a hazard of transfection or transformation, the psoralen photoreaction would be expected to inactivate this free DNA and if anything even more rapidly than it inactivates the RNA-containing virions, thus providing a safety factor not available from conventional inactivating techniques such as heat, alcohol or detergent. Furthermore heat, alcohol or detergent cannot evenly inactivate the RNA and DNA of viruses. (Hanson, 1992)

The kinetic mathematics of psoralen inactivation is frequently nonlinear and can show a "tailing off" effect. This tailing off probably results from loss of psoralen activity during the virus irradiation due to photodegradation of the psoralen itself. Preferably, periodic addition of psoralen during virus inactivation will maintain linear kinetics. The loss of psoralen activity parallels viral inactivation. Two successive steps of irradiation are preferable for effectiveness and for creating higher safety margins for the vaccine. For example, a first exposure of 405 nm wavelength followed by a 365 nm wavelength exposure is preferable for a higher production of cross links capable of disabling a DNA or RNA molecule. In embodiments where a single exposure is required, then a 365 nm wavelength exposure is preferable. The dose rate shall be appropriate for the psoralen absorption under the circumstances; excess dose rate beyond viral inactivation may lead to photodegradation of viral proteins.

Preferably, a sample of the irradiated viral cells may then be cultured and analyzed to ensure inactivation and to eliminate the possibility of residual infectivity.

Treatment of Structural Features that could Impair Immune Response

Regulators of complement activity, such as CD55 and CD59 should preferably be removed from the composition. These surface glycoproteins play a role in inhibiting complement. CD55 destabilizes both C3 convertases (C4b,2b and C3b,Bb) and both C5 convertases (C4b,2b,3b and C3b,Bb,C3b). CD59 and other homologous restriction factors are cell-surface expression proteins that inhibit the intercalation of C9 into the plasma membrane, protecting blood cells, vascular endothelial cells, and other tissues from lytic damage by complement cascade. (Hoffman, 1999) CD55 and CD59 are membrane bound and preferably may be selectively removed by treatment with Phosphatidylinositol-specific Phospholipase C(PI-PLC). This will remove all of the glycosylphosphatidylinositol (GPI) linked proteins, including CD55 and CD59. Such selective enzyme cleavage is among known treatment methods.

Desialation of the inactivated composition is a beneficial step. Preferably, the sialic acid residue from HIV may be removed by treatment with neuraminidase enzyme. Neuramimidase cleaves sialic acid. (Hart, Melanie L., et al., AIDS Res Hum Retroviruses, Vol. 18(17), pp. 1311-7 (2002)) (Meri, 1990) Many of the mannose sugar moieties are protected from the immune system by a coating of sialic acid residue. Sialic acid is found on normal human cells and tissues, and is used by the immune system for "host recognition." In doing so, the immunologic response against "host" structures is limited. Sialic acid residues are also found on the heavily glycosylated envelope of HIV. (Hart, 2002) If the sialic acid residues are removed, then Factor H will not bind to HIV and the vaccine would then be identified as "foreign" by the immune system, so that a robust immunologic response will occur. (Hart, 2002) Other neutralization or desialation methods consistent with the present invention may also be used, such as treatment with trypsin.

In general, treatment of the structural features may be conducted at a variety of points in the preparation of the composition. Desialation is preferable after exposure to psoralen and irradiation with ultraviolet light, in that desialation of active HIV can increase viral replication and infectivity. (Hart, 2002)

Preparation for Administration

The present immunogenic composition may be mixed with appropriate immune stimulant or adjuvant, including those described as alternative embodiments below. Such compositions may be used as are appropriate for the application. Customary stimulants or adjuvant known in the art include incomplete Freund's adjuvant, liposomes, etc. A preferred embodiment includes one or more stimulant taken from customary adjuvants and/or those compositions described further herein.

The immunogenic composition may also be mixed with pharmaceutical or laboratory compositions appropriate for the anticipated method of use or administration, such as carriers or excipients, such as mineral oil.

In one embodiment, the first dose of psoralen vaccine may consist of a solution and/or suspension and/or lyophilized whole inactivated HIV-1 and/or HIV-2 virions. Lyophilization is the creation of a stable preparation of a biological substance by rapid freezing and dehydration of the frozen product under high vacuum, also known as freeze drying whole inactivated HIV-1 and/or HIV-2 virions.

Two sources of HIV virions exist: 1) HIV positive patients, and 2) in vitro cell cultures of HIV. The advantage of the first is the structural and genetic integrity of the virion that has not been comprised by passage through in vitro cell lines. The disadvantage of the first is the possibility of contaminating substances, including other pathogens, HIV derived proteins, host derived proteins, carbohydrates, lipids and nucleic acids of immune and non-immune origin, and anti-microbial elements taken by the host. It is anticipated that all pathogens will be rendered replication incompetent by the psoralen/UV light protocol. An inactivated immunogen, however, can have an immune modulating function that may or may not be beneficial. Since the virus continues to mutate ad infinitum within the host, a lack of homogeneity compromising (theoretically) the ability to reproduce the study will characterize this source of HIV virions. Furthermore, viral proteins such as Tat, Rev, Nef and gp 120 will contaminate the specimen if not properly removed. Methods to separate intact virions from viral proteins do exist, but are not 100% full proof. The above-mentioned contaminated proteins immune suppress the HIV patient and therefore, would likely immune suppress the patient.

Utilizing the second method, the virus will be cultivated and isolated from in vitro cell cultures of stock HIV strains and circulating recombinant forms that have been identified, characterized and sequenced. The genetic content and corresponding protein structure of the whole HIV virion and component parts are published and readily available through multiple sources. Passage of these HIV virions through continuous or non-continuous cell cultures facilitates continual HIV mutation. Therefore, this source of HIV will also be compromised by a lack of homogeneity compromising reproducibility of the study.

A virus is not a homogenous composite of individual replication competent particles. The viral structures are assembled following the same rules of chemistry, physics and math that snowflakes must follow. Therefore, it would be impossible to attain homogeneity of strain of any virus derived from a host animal, cell culture or animal model of that disease. Validation of this concept is found in the Salk and Sabin polio vaccines. Both used in vitro cell cultures of RNA viruses that replicate like HIV at or near the error threshold. Both vaccines, however, were successful, even though one can logically conclude that the virions employed in their vaccination protocols were not mere images of the in vivo viruses afflicting mankind.

Regardless of source, the HIV virions will be photosensitized with one or more psoralens (furocoumarins) and then exposed to ultraviolet A (UVA radiation 320 to 400 nm). Crosslinks and monoadducts of the viral nucleic acids will result effectively eliminating all replication competence.

Following Koch's postulates, any animal with a disease has to be shown to be infected by a specific microorganism. In this situation, the infected "animal" will be the cell culture. It also must be shown that any animal without this microorganism does not have the disease. The infecting organism has to be isolated from the infected animal (in this circumstance the cell culture) and then upon inoculation into another animal (once again in this circumstance the cell culture) infect, replicate and inflict pathogen derived histopathologic changes consistent with the disease under study. Isolation of the pathogen from the second animal (or cell culture in this circumstance) must also be followed by successful tissue cultivation. In this circumstance, after the virus is grown in cell culture, photosensitized with psoralen, exposed to the appropriate wave length and duration of UVA, they must demonstrate no replication competence upon introduction into another cell culture identical to and/or derived from the initial cell culture from which the HIV virions were harvested. This will assure replication incompetence of the immunogen.

Isolation and expansion of HIV, in vitro, can be readily accomplished. Classically, leukocyte enriched whole blood from an HIV negative patient, also known as leukopacks or buffy coats, serve as tissue culture medium. Leukopacks are available from local blood banks.[1] Mass quantification of cell-associated HIV derived virions can be accomplished by the appearance of the p24 gag protein in the culture supernatant.[2] Quantification of cell-free HIV virions can be accomplished by reverse transcriptase activity.[3] Identification of the isolate can be facilitated by determination of syncytium-inducing (SI) isolates versus nonsyncytium-inducing (NSI) phenotypes of HIV can be accomplished using MT-2 cells.[4] Further refinement of virion identification can be accomplished by assessing chemokine coreceptor tropism of the HIV virions using transduced human osteosarcoma (HOS) cells.[5]

[1] Nelson Michael, et al., 1999, HIV Protocols, Chapter 1, pp. 3-10.
[2] Nelson Michael, et al., 1999, HIV Protocols, Chapter 2, pp. 11-15.
[3] Nelson Michael, et al., 1999, HIV Protocols, Chapter 3, pp. 17-22.
[4] Nelson Michael, et al., 1999, HIV Protocols, Chapter 4, pp. 23-27.
[5] Nelson Michael, et al., 1999, HIV Protocols, Chapter 5, pp. 29-33.

Sterility must be assessed and this may be accomplished by incubating the sample, or portion thereof, on a solid or liquid medium for 24-48 hours at 37° C.

Purity may be assessed and accomplished by cesium chloride[6], ultra centrifugation[7], airfuge ultra centrifugation[8], gel electrophoresis[9] and electroelution[10]. Monoclonal antibodies may be used identify and separate the vaccine targeted HIV virions by binding to a specific envelope epitope that is not immunologically cloaked or hidden by tertiary folding and/or glycosylation and is a unique structure found only on this one strain of HIV that is cultivated in the cell culture. This epitope is not found on other wild type or in vitro cell culture derived HIV strains. This will identify the protein fingerprint of the cultivated virus. Structure of the HIV virions can be assessed by infrared and nuclear magnetic resonance as well as mass, ultraviolet and electron spin resonance. Other methods of identifying virion structure, mass, ultraviolet and electron spin can be employed to assure virion identity and (relative) homogeneity. All contaminants of the manufacturing process should be removed.

[6] Botho Bowien, et al., 2003, Nucleic Acids Isolation Methods, Chapter 2, pp. 7-19.
[7] Steven Specter, et al., 2000, Clinical Virology Manual, Third Edition, Chapter 5, pp. 54-65.
[8] Steven Specter, et al., 2000, Clinical Virology Manual, Third Edition, Chapter 5, pp. 54-65.
[9] Botho Bowien, et al., 2003, Nucleic Acids Isolation Methods, Chapter 7, pp. 81-93.
[10] Botho Bowien, et al., 2003, Nucleic Acids Isolation Methods, Chapter 7, pp. 81-93.

Potency may be quantitatively and qualitatively assessed by the capacity of the immunogen to elicit a Th-1 biased immune response in an animal model to the immunogen itself and not a cross-reacting substance.

The bulk quantification of the HIV virions may be deduced by reverse transcriptase activity. The immunogen may then be evenly divided into a defined number of vaccination lots or bottles and properly labeled as far as name, diluent (if applicable), amount of active component per volume, storage instructions, caution notification, site of manufacture, auspices under which the vaccine was prepared, lot designation, control and vial number. In one embodiment, storage conditions, such as temperature and light, may be well defined on the label. Adjuvants, preservatives and included antibiotics, may also be labeled on the vial. Each vial will have temperature sensitive paper attached to it which will change color if the vial has been exposed to temperatures too high or too low.

A standardized DNA fingerprint from the stock HIV virus will be determined and serve as a guide to assess mutation and/or lack thereof in subsequent cell cultures. Prior to the addition of psoralen and exposure to UVA, the RNA from the HIV virions of each cell culture will undergo in vitro reverse transcription into its complimentary DNA and compared to the standardized line. Any significant deviation will be documented and those HIV virions will not be included in the vaccine.

In one embodiment, each vial will also be labeled with date and place of manufacture, expiration date and itinerary (chain of custody), including sites of transport and storage and conditions therein, including temperature and light exposure.

Most importantly, however, is the ability of the inactivated virion to assume the role of a replication competent virion in at least part of the HIV virion life cycle. Only upon doing so will the immunogen be recognizable as foreign and elicit an immunogenic response. The psoralen/UVA inactivated virions must maintain the capability to attach to a target cell and undergo fusion with the target cell plasma membrane. All immunogenic compositions of whole inactivated virions should be subjected to regular in vitro testing, preferably with peripheral blood mononuclear cells from HIV negative donors. The ability to attach to and be assimilated into the target cell stands testimony to the structural and functional integrity of the immunogen.

The biological activity of the immunogen can be quantified by a variety of ratios based upon a simple arithmetic equation: total number of virions (TV) equal number of free unattached virions (FV) plus the number of attached virions (AV) noted in an in vitro peripheral blood mononuclear cell culture derived from an HIV negative patient.

TV=FV+AV. TV can be calculated with knowledge of the average molecular weight (AMW) of an HIV virion. The weight of a pure or near pure HIV immunogen (WHI) source can be determined. WHI/AMW=TV. Monoclonal antibodies can be utilized to separate out the unattached virions (FV) from the attached virions (AV) and quantify directly FV and indirectly AV. Well-defined calcium fluxes will occur upon virion binding. A multiplicity of methods exists to separate metabolically active from inactive T and B cells. This would serve to define AV directly.

Therefore, the biological activity of the psoralen immunogen can be determined directly and indirectly from the above equations. Preferably, the immunogen will have an AV/TV ratio of 0.8 or greater. Other ratios may be used.

Samples of every lot dispensed for human use, animal model use, in vitro experimentation and cell culture may be preserved in glycerol and placed under dry ice (solid $CO_2$) conditions at −70° C. in perpetuity.

Sample Protocol III

Patient Selection—Exclusion Criteria:

1. Active infection either acute or chronic (a trial involving only HIV patients can be performed, but must be separate from those that are HIV negative)
2. Any auto-immune disorder, including eczema and psoriasis
3. Malnourished patients, including anorexia, bulimia, kwashiorkor, vitamin or mineral deficiencies
4. Active malignancy or history of malignancy
5. Prior participation in any drug or vaccine trial
6. Prior significant irradiation exposure
7. Any immunosuppressive diseases
8. Chronic use of any prescribed medication
9. Mastocytosis
10. Carcinoid
11. Psychiatric disturbances
12. Patients with undefined prior medical history
13. Asthma
14. History of drug sensitivities
15. Addison's disease
16. Crohn's disease
17. Hypothyroidism
18. Hyperthyroidism
19. Hypoparathyroidism
20. Hyperparathyroidism
21. Pregnancy or possibility occurring during course of the trial. All women of child bearing potential who wish to participate in the trial must either be celibate or use a reliable, definable method of birth control that is documented by a member of the research team.
22. Growth hormone deficiency or acromegaly.
23. Diabetes mellitus
24. Diabetes insipidus
25. Asplenic patients
26. Sickle cell disease
27. Any hemoglobinopathy
28. Any organ disease, including cardiac, hepatic, renal, intestinal, etc.
29. Patients planning on travelling out of range of the treatment facility
30. People involved in administering this program or families thereof
31. Prior history of STDs
32. Down syndrome or other chromosomal aberrations
33. Multiple dystrophy or other genetic disorders
34. Eosinophilia and/or increase in basophils found in whole blood Patient Selection—Inclusion Criteria 1. Must understand and agree to all aspects of the Informed Consent
2. Age 2-30 at time of protocol commencement. Ideal age 16-18.
3. Must not have any exclusion criteria
4. Must be available at all planned intervention times and be willing to meet at other times PRN
5. Must be willing to document and share any and all possible adverse reactions
6. Must be willing to document and share information on all sexual contacts before and after trial. All sexual contacts must be tested for all forms of STDs
7. PPD negative
8. Have positive responses to control recall antigen influenza virus (demonstrates intact Th-1 immune repertoire)
9. Have positive responses to control recall tetanus toxoid (demonstrates intact Th-2 immune repertoire)
10. Must be ambulatory Method of Vaccination Intradermally or orally.

Preferred Site of intradermal vaccination.

Upper medial thigh (clothed area, non-UV irradiated) drains into Peyer's patches Vaccine Site Preparation Shave area to be vaccinated approximately 24 hours before vaccine administration. This will stimulate the skin to become a tertiary lymphatic tissue facilitating vaccine assimilation and processing. Just prior to vaccine administration, a blood pressure cuff over the proximal thigh inflated to approximately 20 mm of mercury for 20 minutes (increases venous pressure which leads to increased lymphatic flow). Just prior to and after vaccine administration, site should be warmed and exercised.

Caring for Vaccination Site After Administration

Patient prohibited from bathing or cleansing the site or to go swimming for 12 hours Exclusion Criteria of Vaccine Site Recent skin lacerations, breaks, contusions or bruising Active skin infection: bacteria, fungus, Candida, virus (warts)

Timing of Vaccinations

Day 1, 30, and 180. Alternatively, Day 1, 20-40, and 160-200

Adjuvants

An adjuvant is administered before, simultaneous with or after each dose of the immunogenic compositions. Adjuvants are used to promote a Th-1 and include a leukotriene receptor antagonist such as Montelukast, a mast cell and basophil stabilizer such as Cromolyn, and prostaglandin synthetase inhibitors such as Indomethacin.

Specific Additional Lab Tests to be Performed on All Participants $IgG_1$, $IgG_2$, $IgG_3$, $IgG_4$ titers to the subunit vectors ($IgG_1$ and $IgG_3$ facilitate a Th-1 response and $IgG_2$ and $IgG_4$ facilitate a Th-2 response), as well as IgA, IgM and IgE titers to the subunit vectors. IgM is indicative of an acute immunologic response to a pathogen or pathogen-derived protein in an immunologically naive patient (no prior immune response to the specific pathogen or pathogen epitope). IgE would be indicative of an allergic, Th-2 mediated immunologic response. IgA would, in most circumstances, be consistent with a Th-2 response.

Conduct qualitative and quantitative cytotoxic T cell assays to the subunit vectors according to standardized procedures known in the art.

Dates Tests to be Performed

Testing will be done immediately prior (approximately one week) to each vaccine administration. Any response consistent with a Th-2 bias would eliminate that patient from further trial participation.

Sample Protocol IV:

Dosing of Vaccines

Targeting dose for an adult (age >16) male or female will contain between $1x10^9$ and $1x10^{10}$ HIV biologically active fusion peptides. The second dosage will be $1/10^{th}$ of the initial vaccination. The third dosage will be $1/100^{th}$ of the initial vaccination. Adolescent patients from age 8-15 would receive one-half (½) of the above doses. Pediatric patients would receive one-fourth (¼) of the above dosing schedule.

In one embodiment a first vaccine will consist of X concentration of HIV-1 fusion or matrix protein polypeptide or Y concentration of the corresponding nucleic acid sequence combined with a pharmaceutically acceptable carrier. The precise dosing will depend upon the patient's age, weight, and gender. The second vaccine will consist of $1/10^{th}$ of both X and Y concentrations. The third vaccine will consist of $1/100^{th}$ of X and Y concentrations. This will facilitate a Th-1 response.

In one embodiment for administration of psoralen inactivated HIV, the first vaccine will consist of [X] concentration of an ultraviolet radiation and psoralen inactivated HIV virus combined with a pharmaceutically acceptable carrier. The precise dosing would depend upon the patient's age, weight and gender. The second vaccine will consist of $1/10^{th}$ of [X] concentration. The third vaccine will consist of $1/100^{th}$ of [X] concentration. This will facilitate a Th-1 response.

With each administration protocol, Th-1 immune responses to the immunogenic compositions are monitored. The 3X cycle will repeat until a Th-1 immune response is observed. At that point, the immunogenic composition administered would then decline by a factor of 10 for two more vaccination procedures.

The purpose of eliciting an immunologic response is to cultivate memory cells specific for the immunogen(s). With each vaccine administration, memory cells are activated. Memory cells require smaller amounts of antigen to proliferate than naive inactivated T cells. Therefore, subsequent follow-up vaccination efforts require fewer antigens than the initial vaccination. Also, the basic concept that the least amount of antigen with the shortest half-life is most likely to elicit a Th-1 response holds true with initial exposure to the immunogen as well as subsequent re-exposures.

The above administration and dosing regimen of an immunogenic composition based on HIV fusion protein, matrix protein or psoralen inactivated HIV are illustrated in FIG. 2 in a flowchart.

Sample Protocol V:

In one embodiment, lymphatic targeting of the vaccine may be selected. Lymphatic tissue is a site of over 90% of all white blood cells. The turbulence within the arterial arm of the vascular system created by the high pressure is not conducive for immune function. The low pressure within the venous system is still not optimal for activation and functions of white blood cells and complement proteins, due to high flow velocity. Within the lymphatic tissue, not only is the pressure low, but the flow velocity is minimal. Approximately 3 liters of fluid percolate through the left thoracic duct per day and 1 liter through the right thoracic duct. Inserting a plastic cannula into a lymphatic vessel on the dorsal surface of the foot, as well as elsewhere on the lower extremity, can be accomplished for vaccine administration. This is a tedious, time consuming and somewhat uncomfortable procedure, and requires a skillful, competent, conscientious technician.

Sample Protocol VI:

In one embodiment, after proper patient selection, patient preparation commences. To enhance a Th-1 response, the patient should receive, for one month, the following medications: (1) Montelukast, (2) Cromolyn, and (3) Indomethacin. Indomethacin is a prostaglandin synthetase inhibitor. Montelukast is a leukotriene blocker and Cromolyn stabilizes mast cells and basophils. Leukotrienes mediate inflammatory, Th-2 responses. Mast cells and basophils facilitate Th-2/allergic responses. Prostaglandins are implicated in the inflammatory response that characterizes a Th-2 response. In the Th-1 versus Th-2 paradigm, a see-saw can be envisioned. By dampening the Th-2 response, the Th-1 response will be enhanced.

Sample Protocol VII:

Louis Pasteur created the second vaccine for human use. It was predominantly used to prevent the development of rabies after exposure. Initially, he administered a replication incompetent "dead vector." The vaccine was administered daily for approximately two weeks. Viability of the virus was temporized in vitro. After administration of the dead vector, he administered weakened but replication competent virus to the recipient. Finally, on the last day of the series of vaccines, he administered live replication competent non-attenuated rabies virus.

It appears the first immunization consisted of virus grown in culture for 14 days and was replication incompetent. The second immunization consisted of virus grown in culture for 13 days and demonstrated minimal replication capability. The third immunization consisted of virus grown in culture for 12 days and demonstrated replication capability that was impaired, but greater than that administered in the second series. This continued on for approximately 14 days. It appears Pasteur did not administer each vaccination compilation.

In one embodiment, an administration protocol for a vaccine based on psoralen inactivated HIV may include gradually ramping up the replication competence of the immunogen until administration of a live wild type virus to the vaccine as described above.

The serious consequences of administering a live non-attenuated HIV virus as a vaccine are known in the art. Therefore, in one embodiment an administration protocol for a vaccine based on psoralen inactivated HIV may be prophylactic. That is designed for HIV negative patients. In another embodiment, an administration protocol for a vaccine based on psoralen inactivated HIV may be therapeutic. That is designed for HIV positive patients.

Sample Protocol VIII:

Selection of Culture Material and Strain(s) of HIV Virus;

HIV live vectors may be purchased and used as sources of vaccine material from the various sources including but not limited to the national Institute of Health (NIH). These viral isolates lack many of the characteristics noted in actively infected patients since they have been passed through numerous cell lines in vitro. Quite typically, continuous cells lines (cells which have no finite end to the number of mitotic divisions possible) are used as a culture medium due to their universal availability, low cost, well defined nutrient needs and overall predictability.

The predictability of continuous cell cultures is defined by three parameters: 1) Infinite number of mitosis; 2) Short G1 phase of the cell cycle allowing cell division within hours or even minutes; and 3) Continual mutation. The virus, however, quickly adapts to the host environment. Continuous human T cell lines such as SupT1, H9, Jurkat or A3.01 can also be obtained from the NIH AIDS Research and Reference Reagent Program or the American Type Culture Collection, both in Rockville, Md. Laboratory adapted HIV viruses can propagate in these continuous cell lines but most viral isolates of human origin do not.[11]

[11] Nelson Michael, et. al., 1999, HIV Protocols, Ch. 19, pp. 185-196

Classical virology distinguishes between "wild-type" virus and mutated or otherwise altered viral material. In actuality though a "wild-type" virus may not be and often is not synonymous with virus isolated from an intact host. Therefore, a distinction needs to be made between laboratory derived "wild-type" usually produced by passage through continuous cell cultures and viral isolates from the intact natural host. The latter are best referred to as field or clinical isolates and demonstrate the structural or genetic qualities that need to be mirrored in an appropriate vaccine.

Within an intact host the HIV virus inhabits multiple spheres, organ systems, histological tissues and is excreted in various cellular fluids in part or in whole. The actual HIV virus, as well as intact RNA and DNA sequences, can be recovered from infected patients at all stages of the disease spectrum even before the acute retroviral syndrome which occurs in most patients within 30 days of infection. As mentioned, the virus adapts to its host environment and with a half-life of six hours a typical HIV virus would be produced and secreted by cells in the same tissue that it ultimately re-infects. Therefore, viral cultures in different organ systems of the same patient often demonstrate subtle but important genotypic and phenotypic differences which are necessary for viral replication in the tissue it infects. This is an extrapolation on basic Darwinian principles that an organism will adapt to its environment or perish. The immunological milieu of the human host is divided into several separate biospheres or compartments (all of which become HIV infected) including but not limited to the gut associated lymphoid tissue (GALT), bronchial associated lymphoid tissue (BALT), skin associated lymphoid tissue (SALT), mammary associated lymphoid tissue (MALT) and conjunctival associated lymphoid tissue (CALT). The lymphocytes and other cellular as well as other molecular components of the immune system are not evenly distributed throughout the somatic tissues.[12] The immune pressure on the HIV virus, therefore, differs with its specific tissue or organ of origin. The genotypic and phenotypic expression of the virus will reflect the immune environment it propagates in. Genotypic and phenotypic differences of HIV have been observed in the same patient in different immune environments. The HIV cultured from transmission fluids would be the most logical starting source for virus isolation for vaccine manufacture.

[12] John A. Parrish, et. al., 1983, Photoimmunology, Chap. 6, pp. 95-130

The primary method of HIV transmission is sexual. Therefore the seminal, vaginal and rectal fluids would be the most logical point source for obtaining viral field or clinical isolates for vaccine production. Methods of specimen collection by cervicovaginal lavage are well defined. Manual collection of cervical secretions has also been delineated. This is an alternative method of obtaining either whole replication competent virions, viral RNA or DNA. Viral isolation from seminal fluid is also routinely performed.[13] Methods of culturing HIV-1 in human semen are standard in the industry.[14] Finally, the process of collection and processing of rectal secretions has been defined in the literature.[15]

[13] Nelson Michael, et. al., 1999, HIV Protocols, Ch. 17, pp. 151-164

[14] Nelson Michael, et. al., 1999, HIV Protocols, Ch. 8, pp. 51-57

[15] Nelson Michael, et. al., 1999, HIV Protocols, Ch. 35, pp. 323-327

Detection, isolation and expansion of the HIV virus can be performed on a variety of infected tissues including, but not limited to, human monocytes/macrophages, T cells and central nervous system tissue.[16] HIV culture and expansion can be accomplished with mitogen—stimulated peripheral blood mononuclear cells (PBMCs) from “normal” uninfected healthy donors.[17] This process, although the cornerstone of many HIV vaccine and drug efforts, is perilous. The virus will continue to mutate in cell culture and will quickly assume genotypic and phenotypic characterizations (genetic drift) that differentiate it from the original tissue isolate. Cultures are also unreliable and often require 30 days before detectable viral replication is noted.

[16] Nelson Michael, et. al., 1999, HIV Protocols, Ch. 9 & 10, pp. 61-81

[17] Nelson Michael, et. al., 1999, HIV Protocols, Ch. 1, pp. 3-10

Starting materials for isolation of viral nucleic acids can be divided into two broad categories: 1) cell rich; and 2) cell poor. Some overlap in these categories does exist. A cell poor isolate can be obtained from an initial cell rich culture. Cell rich starting materials include but are not limited to the following: 1) whole blood or blood fractions; 2) Bone marrow; 3) Tissue specimens, fresh, frozen, paraffin embedded or otherwise prepared; 4) In vitro cultured cells 5) Swabs impregnated with tissue derived fluids and cells; 6) Bronchial lavage; 7) Semen; and/or 8) Vaginal wall and cervical, uterine scrapings. Cell poor starting materials include but are not limited to the following: 1) blood plasma; 2) Blood serum; 3) Urine; 4) Saliva; 5) Cell culture supernatants; 6) Stool; 7) Seminal fluids; 8) Vaginal fluids.[18]

[18] Botho Bowien, et. al., 2003, Nucleic Acids Isolation Methods, Ch. 5, pp. 53-59

Viruses including HIV can be isolated from either category of startup materials. However, isolation of viral DNA from cell rich materials will be complicated by the co-purification of host and viral DNA. PCR based technology as discussed below can detect, isolate and amplify viral nucleic acid from cell rich cultures, but this requires a large amount of nucleic acid as template and this requirement may inhibit PCR.[19] Viral DNA/RNA in cell rich medium is both cell associated and cell free. In the intracellular compartment viral nucleic acids may be integrated into the host genome or bound to host and/or viral proteins in both the cytoplasmic and nuclear compartments. Finally, nucleic acids in part or whole can be found in a cell rich system in the extracellular milieu protein free. Therefore, in a cell rich medium, the source and content of viral DNA is not uniform.

[19] Botho Bowien, et. al., 2003, Nucleic Acids Isolation Methods, Ch. 5, pp. 53-59

Cell free body fluids limit but do not completely eliminate host DNA contaminant. Viral DNA content in many cell poor isolates is characteristically of low titer necessitating concentration of nucleic acids before isolation and amplification.

Erythrocytes from mammals are enucleated shortly after entering the circulation and therefore have very little DNA. Mitochondrial DNA is still found within the mitochondria but in an intact cell containing a nucleus the mitochondrial DNA is a very small fraction of the total cellular DNA. Human blood contains approximately 1000 times more erythrocytes than leukocytes which have nuclei. Therefore, if blood is used as a selective medium for viral isolation and amplification the erythrocytes should be removed first. This can be accomplished by hypotonic shock since red blood cells burst more rapidly in a hypotonic medium than white blood cells. Ficoll-density-gradient centrifugation can separate mononuclear cells (lymphocytes and monocytes) from erythrocytes as well. Finally, centrifuging whole blood at 3300 g for ten minutes at room temperature separates the blood into three readily discernable fractions: (1) white blood cell enriched fraction known as the buffy coat. (2) Blood plasma. (3) Red blood cells.[20] The buffy coat would be a cell rich source suitable for viral nucleic acid separation and the blood plasma fraction would serve as a cell poor medium also suitable for viral nucleic acid separation.

[20] Botho Bowien, et. al., 2003, Nucleic Acids Isolation Methods, Ch. 2, pp. 7-19

Selection of viral strains logically parallels those strains indigenous in the population. As mentioned above, a single clone of virus would not be representative of the HIV epidemic. Other factors to be considered include but are not limited to the immunogenicity and pathogenicity of individual HIV strains. Recently, HIV-1-M subtype C has emerged as a predominant strain in various areas of the globe. HIV-1 C is the most commonly transmitted subtype worldwide and predominates in Southern Africa, India, China and Brazil. This strain is more virulent and easier to transmit by sexual intercourse than other isolated strains. The 5' LTR possesses three $NF_\kappa B$ binding sites and may in part or whole explain the enhanced virulence and ease of transmission of this strain. Other possible explanations for this subtype emerging as the leading strain of HIV worldwide include a prematurely truncated Rev protein, a 5-amino acid insertion into the Vpu protein and a more efficient protease enzyme. The HIV-1 C protease is distinct in primary, secondary, tertiary and quaternary structure. Specifically, the hinge region and the α-helix of HIV-1 C have been linked to increased protease activity. Finally, variation in the HIV-1 C protease specific cleavage sites has been linked to enhanced viral transmissibility and virulence.[21]

[21] Tulio de Oliveira, et al., 2003, Variability at Human Immunodeficiency Virus Type 1 Subtype C Protease Cleavage Sites: an Indication of Viral Fitness?, Journal of Virology, pp. 9422-9430, September 2003.

In one embodiment, a vaccine may be comprised of the elements that most closely mirror the actual infectious particle or portion thereof. This should reflect the quasi-species genotypic and phenotypic variance noted in the intact host. The virions used for vaccine manufacture can come from any tissue source but seminal, vaginal and/or rectal tissue are targeted in one embodiment. Field or clinical isolates of the virus differ genotypically and phenotypically from isolates passed through in vitro cell cultures.

Without departing from the scope thereof, one skilled in the art can easily ascertain from the following descriptions, the essential characteristics of this invention to adapt it. The following descriptions and examples are set forth merely to illustrate the invention and are not intended to be limiting. Because modifications of the disclosed embodiments incorporating the spirit and substance of the invention may occur to persons skilled in the art, the invention should be construed to include everything within the scope of the appended claims and equivalents thereof. The patents, patent application publications and other publications referenced herein are incorporated in their entirety.

What is claimed is:

1. A method of stimulating a Th-1 immune response to human immunodeficiency virus type 1 (HIV-1) in a mammalian subject, which method comprises:
   i) Administering to the mammalian subject at least three doses of an immunogenic composition wherein the immunogenic composition comprises a whole inactivated HIV-1 virus, wherein the virus has been inactivated by exposure to ultraviolet radiation and psoralen, lacks CD55 and CD59 in the viral membrane and has been subjected to desialation, and wherein the time between administration of the first and second doses of the immunogenic composition is from 1 to 20 days and the time between administration of the second and third doses is from 120 to 180 days; further wherein each dose of the immunogenic composition is a ten fold dilution in concentration of the previous dose; and
   ii) Administering to the mammalian subject an adjuvant to boost the Th-1 immune response, wherein the time between the first and second administration of the adjuvant is from 1 to 20 days and the time between the second and third administration is from 120 to 180 days.

2. A method according to claim 1, wherein the starting dose of the inactivated HIV virus is $1 \times 10^9$-$1 \times 10^{10}$ virions.

3. A method according to claim 1, wherein the adjuvant is a leukotriene receptor antagonist.

4. A method according to claim 2, wherein the leukotriene receptor antagonist is Montelukast.

5. A method according to claim 1, wherein the adjuvant is a mast cell and basophil stabilizer.

6. A method according to claim 5, wherein the mast cell and basophil stabilizer is Cromolyn.

7. A method according to claim 1, wherein the adjuvant is a prostaglandin synthetase inhibitor.

8. A method according to claim 1, wherein the prostaglandin synthetase inhibitor is Indomethacin.

9. A method according to claim 1, wherein the site of administration of the immunogenic composition is one that targets lymphatic tissue.

10. A method according to claim 1, wherein the administering to the mammalian subject at least three doses of an immunogenic composition is repeated until a Th-1 immune response is detected.

11. A method according to claim 1, wherein the immunogenic composition is administered, by capsule, gelcap, tablet, enteric capsule, encapsulated particle, powder, suppository, injection, ointment, cream, implant, patch, liquid, inhalant, or spray.

12. A method according to claim 1, wherein the immunogenic composition is administered, orally, transbucally, transmucosally, sublingually, nasally, rectally, vaginally, intraocularly, intramuscularly, intralymphatically, intravenously, subcutaneously, transdermally, intradermally, intra tumor, topically, transpulmonarily, by inhalation, by injection, or by implantation.

* * * * *